United States Patent
Norman

(10) Patent No.: US 8,372,382 B2
(45) Date of Patent: Feb. 12, 2013

(54) SKIN MOISTURIZER AND AGE FIGHTING FORMULA

(75) Inventor: Greg Norman, Bedford, TX (US)

(73) Assignee: Mary Kay, Inc., Dallas, TX (US)

( * ) Notice: Subject to any disclaimer, the term of this patent is extended or adjusted under 35 U.S.C. 154(b) by 0 days.

(21) Appl. No.: 13/320,125

(22) PCT Filed: Oct. 3, 2011

(86) PCT No.: PCT/US2011/054633
§ 371 (c)(1), (2), (4) Date: Nov. 11, 2011

(87) PCT Pub. No.: WO2012/045081
PCT Pub. Date: Apr. 5, 2012

(65) Prior Publication Data
US 2012/0294814 A1   Nov. 22, 2012

Related U.S. Application Data

(60) Provisional application No. 61/388,893, filed on Oct. 1, 2010.

(51) Int. Cl.
*A61K 8/00* (2006.01)
*A61K 8/06* (2006.01)

(52) U.S. Cl. .......................................... 424/59

(58) Field of Classification Search ................ None
See application file for complete search history.

(56) References Cited

U.S. PATENT DOCUMENTS

| | | | |
|---|---|---|---|
| 5,663,213 A | 9/1997 | Jones et al. | 523/105 |
| 6,384,104 B1 | 5/2002 | Chang et al. | 523/105 |
| 6,451,339 B2 | 9/2002 | Patel et al. | 424/451 |
| 6,488,941 B1 | 12/2002 | Burnier et al. | 424/401 |
| 6,831,107 B2 | 12/2004 | Dederen et al. | 514/777 |
| 7,146,719 B2 | 12/2006 | Iha | 29/830 |
| 7,262,180 B2 * | 8/2007 | Mastrodonato et al. | 514/54 |
| 2004/0247543 A1 | 12/2004 | Huerta et al. | |
| 2005/0031655 A1 | 2/2005 | Karpov | |
| 2006/0093636 A1 | 5/2006 | Farber | |
| 2008/0145452 A1 | 6/2008 | Lichtblau et al. | 424/642 |
| 2008/0181858 A1 | 7/2008 | Davis et al. | |
| 2009/0202459 A1 | 8/2009 | Spaulding | 424/60 |

FOREIGN PATENT DOCUMENTS

| | | |
|---|---|---|
| EP | 1459736 | 9/2004 |
| WO | WO 97/40816 | 11/1997 |
| WO | WO 97/40817 | 11/1997 |

OTHER PUBLICATIONS

International Search Report and Written Opinion, issued in International Patent Application No. PCT/US2011/054633, mailed on May 31, 2012.

* cited by examiner

*Primary Examiner* — Anand Desai
*Assistant Examiner* — Melissa Mercier
(74) *Attorney, Agent, or Firm* — Fulbright & Jaworski L.L.P.

(57) ABSTRACT

Disclosed is a non-ionic oil-in water emulsion comprising less than 50% by weight of water, a combination of non-ionic emulsifiers and non-ionic emulsion stabilizers, a combination of humectant skin conditioning agents, and a combination of UV absorbing agents. The emulsion can be stable and have an SPF of at least 30.

18 Claims, No Drawings

SKIN MOISTURIZER AND AGE FIGHTING FORMULA

CROSS REFERENCE TO RELATED APPLICATIONS

This application is a national phase application under 35 U.S.C. §371 of International Application No. PCT/US2011/054633, filed Oct. 3, 2011, which claims the benefit of U.S. Provisional Application No. 61/388,893, filed Oct. 1, 2010. The contents of the referenced applications are incorporated by reference.

BACKGROUND OF THE INVENTION

A. Field of the Invention

The present invention relates generally to compositions that can be used to improve the skin's visual appearance. In particular, the present invention concerns topical skin care compositions that include a combination of non-ionic surfactants, a combination of humectant skin conditioning agents, and a combination of sunscreen agents. A particular use for the composition can be to moisturize skin or treat dried, chapped, or flaky skin, to treat fine lines and wrinkles, or to protect the skin from UV radiation.

B. Description of Related Art

Several skin moisturizing compositions are currently available. These compositions have various drawbacks ranging from unpleasant tactile properties (e.g., heavy, greasy, or sticky feel), low staying power (e.g., tendency to migrate and pool from point of application or tendency to be easily removed from the skin via being subjected to only one washing), insufficient moisturization and/or UV protection capabilities.

SUMMARY OF THE INVENTION

The present invention overcomes deficiencies in the art by providing a cosmetically elegant composition that is in the form of a stable non-ionic oil-in-water formulation having skin moisturization capabilities.

In one aspect of the present invention, there is disclosed a non-ionic oil-in water emulsion comprising less than 50% by weight of water and great than 10%, 20%, 30%, or 40% by weight of water, a combination of non-ionic emulsifiers and non-ionic emulsion stabilizers comprising, glyceryl stearate, PEG-100 stearate, arachidyl glucoside, and arachidyl alcohol, a combination of humectant skin conditioning agents comprising glycereth-26, glycerin, betaine, panthenol, and allantoin, and combination of UV absorbing agents comprising homosalate, octisalate, oxybenzone, avobenzone, octocrylene, and styrene/acrylates copolymer, wherein the emulsion is stable and includes an SPF of at least 30. The emulsion can have a ratio of the total amount of water (w/w) to the total amount of the combination non-ionic emulsifiers and non-ionic emulsion stabilizers (w/w) that ranges from 18:1 to 23:1 or from 20:1 to 22:1, the ratio of the total amount of water (w/w) to the total amount of the combination of humectant skin conditioning agents (w/w) ranges from 4:1 to 8:1 or from 5:1 to 7:1, and/or the ratio of the total amount of water (w/w) to the total amount of the combination of UV absorbing agents (w/w) ranges from 2:1 to 3:1. In certain aspects, the ratio of the total amount of the combination of humectant skin conditioning agents (w/w) to the total amount of the combination non-ionic emulsifiers and non-ionic emulsion stabilizers (w/w) ranges from 2:1 to 5:1 or from 3:1 to 4:1. The ratio of the total amount of the combination of UV absorbing agents (w/w) to the total amount of the combination of humectant skin conditioning agents (w/w) can range from 1:1 to 4:1 or from 2:1 to 3:1. The ratio of the total amount of the combination of UV absorbing agents (w/w) to the total amount of the combination non-ionic emulsifiers and non-ionic emulsion stabilizers (w/w) can range from 7:1 to 10:1 or from 8:1 to 9:1. In one embodiment, the emulsion comprises 45-49% by weight of water, 2-3% by weight of the combination of glyceryl stearate, PEG-100 stearate, arachidyl glucoside, and arachidyl alcohol, 7-9% by weight of the combination of glycereth-26, glycerin, betaine, panthenol, and allantoin, and 18 to 22% by weight of the combination of homosalate, octisalate, oxybenzone, avobenzone, octocrylene, and styrene/acrylates copolymer. The emulsion can include 0.8 to 1% by weight of glyceryl stearate, 0.5 to 0.7% by weight of arachidyl alcohol, 0.5 to 0.7% by weight of PEG-100 stearate, and 0.1 to 0.3% by weight of arachidyl glucoside. In another aspect, the emulsion can include 3 to 5% by weight of glycereth-26, 2 to 4% by weight of glycerin, 0.1 to 2% by weight of betaine, 0.01 to 1% by weight of panthenol, and 0.01 to 1% by weight of allantoin. In still another aspect, the emulsion can include 4 to 6% by weight of homosalate, 4 to 6% by weight of octisalate, 3 to 5% by weight of oxybenzone, 1 to 3% by weight of avobenzone, 1 to 3% by weight of octocrylene, and 1 to 3% by weight of styrene/acrylates copolymer. The emulsion can have a non-oily feel and/or a silky texture.

Also disclosed is a method for moisturizing skin using any of the compositions disclosed throughout this specification. The method can include topically applying a composition to skin in need of moisturization. In one aspect, the composition is applied to dry, flaky, or cracked skin. The composition can moisturize the skin for at least 1, 2, 3, 4, 5, 6, 7, 8, 9, 10, 11, or 12 hours after topical application. In certain aspects, the composition remains on the skin after the skin has been washed at least two times, which confirms the composition's substantive properties or abilities to remain on the skin despite washing, rubbing, or otherwise touching the composition while the composition is on the skin. This substantive property is a technical achievement in that it can reduce the amount of composition that a user ultimately has to apply to skin, continuously protect skin, and/or continuously moisturize skin without fearing that the composition wears-off within 1, 2, 3, 4, 5, 6, 7, 8, 9, 10, 11, or 12 hours after application to skin. In this sense, the composition is a substantive long-lasting composition. The composition can be applied to facial skin, neck skin, arm skin, hand skin, chest skin, back skin, leg skin, feet skin, skin around the periorbital region of the face, etc.

In one aspect of the present invention there is disclosed a non-ionic oil-in water emulsion comprising 40-50% by weight of water, a combination of non-ionic emulsifiers and non-ionic emulsion stabilizers comprising glyceryl stearate, PEG-100 stearate, arachidyl glucoside, and arachidyl alcohol, a combination of humectant skin conditioning agents comprising glycereth-26, glycerin, betaine, panthenol, and allantoin, and a combination of UV absorbing agents comprising homosalate, octisalate, oxybenzone, avobenzone, octocrylene, and styrene/acrylates copolymer, wherein the emulsion is stable and includes an SPF of at least 30, wherein the ratio of the total amount of water (w/w) to the total amount of the combination non-ionic emulsifiers and non-ionic emulsion stabilizers (w/w) ranges from 18:1 to 23:1 or from 20:1 to 22:1, wherein the ratio of the total amount of water (w/w) to the total amount of the combination of humectant skin conditioning agents (w/w) ranges from 4:1 to 8:1 or from 5:1 to 7:1, and wherein the ratio of the total amount of water (w/w) to the total amount of the combination of UV absorbing agents (w/w) ranges from 2:1 to 3:1.

In another aspect, there is disclosed a non-ionic oil-in water emulsion comprising 40-50% by weight of water, a combination of non-ionic emulsifiers and non-ionic emulsion stabilizers comprising a combination of humectant skin conditioning agents, and a combination of UV absorbing agents, wherein the emulsion is stable and includes an SPF of at least 30, wherein the ratio of the total amount of water (w/w) to the total amount of the combination non-ionic emulsifiers and non-ionic emulsion stabilizers (w/w) ranges from 18:1 to 23:1 or from 20:1 to 22:1, wherein the ratio of the total amount of water (w/w) to the total amount of the combination of humectant skin conditioning agents (w/w) ranges from 4:1 to 8:1 or from 5:1 to 7:1, and wherein the ratio of the total amount of water (w/w) to the total amount of the combination of UV absorbing agents (w/w) ranges from 2:1 to 3:1.

In still another embodiment there is disclosed a non-ionic oil-in water emulsion comprising 40-50% by weight of water, a combination of non-ionic emulsifiers and non-ionic emulsion stabilizers comprising glyceryl stearate, PEG-100 stearate, arachidyl glucoside, and arachidyl alcohol, a combination of humectant skin conditioning agents comprising glycereth-26, glycerin, betaine, panthenol, and allantoin, and a combination of UV absorbing agents comprising homosalate, octisalate, oxybenzone, avobenzone, octocrylene, and styrene/acrylates copolymer, wherein the emulsion is stable and includes an SPF of at least 30, wherein the ratio of the total amount of the combination of humectant skin conditioning agents (w/w) to the total amount of the combination non-ionic emulsifiers and non-ionic emulsion stabilizers (w/w) ranges from 2:1 to 5:1 or from 3:1 to 4:1, wherein the ratio of the total amount of the combination of UV absorbing agents (w/w) to the total amount of the combination of humectant skin conditioning agents (w/w) ranges from 1:1 to 4:1 or from 2:1 to 3:1, and wherein the ratio of the total amount of the combination of UV absorbing agents (w/w) to the total amount of the combination non-ionic emulsifiers and non-ionic emulsion stabilizers (w/w) ranges from 7:1 to 10:1 or from 8:1 to 9:1.

Also disclosed is a non-ionic oil-in water emulsion comprising, 40-50% by weight of water, a combination of non-ionic emulsifiers, a combination of humectant skin conditioning; and a combination of UV absorbing agents, wherein the emulsion is stable and includes an SPF of at least 30, wherein the ratio of the total amount of the combination of humectant skin conditioning agents (w/w) to the total amount of the combination non-ionic emulsifiers and non-ionic emulsion stabilizers (w/w) ranges from 2:1 to 5:1 or from 3:1 to 4:1, wherein the ratio of the total amount of the combination of UV absorbing agents (w/w) to the total amount of the combination of humectant skin conditioning agents (w/w) ranges from 1:1 to 4:1 or from 2:1 to 3:1, and wherein the ratio of the total amount of the combination of UV absorbing agents (w/w) to the total amount of the combination non-ionic emulsifiers and non-ionic emulsion stabilizers (w/w) ranges from 7:1 to 10:1 or from 8:1 to 9:1.

In even another embodiment there is disclosed a non-ionic oil-in water emulsion comprising 45-49% by weight of water, 2-3% by weight of the combination of glyceryl stearate, PEG-100 stearate, arachidyl glucoside, and arachidyl alcohol, 7-9% by weight of the combination of glycereth-26, glycerin, betaine, panthenol, and allantoin, and 18 to 22% by weight of the combination of homosalate, octisalate, oxybenzone, avobenzone, octocrylene, and styrene/acrylates copolymer, wherein the emulsion is stable and includes an SPF of at least 30. The emulsion can include 0.8 to 1% by weight of glyceryl stearate, 0.5 to 0.7% by weight of arachidyl alcohol, 0.5 to 0.7% by weight of PEG-100 stearate, 0.1 to 0.3% by weight of arachidyl glucoside, 3 to 5% by weight of glycereth-26, 2 to 4% by weight of glycerin, 0.1 to 2% by weight of betaine, 0.01 to 1% by weight of panthenol, 0.01 to 1% by weight of allantoin, 4 to 6% by weight of homosalate, 4 to 6% by weight of octisalate, 3 to 5% by weight of oxybenzone, 1 to 3% by weight of avobenzone, 1 to 3% by weight of octocrylene, and 1 to 3% by weight of styrene/acrylates copolymer.

In one instance, there is disclosed a non-ionic oil-in water emulsion comprising, consisting essentially of, or consisting of the ingredients and amounts of such ingredients disclosed in Table 1 or Table 2, both of which are incorporated into this section by reference.

In certain embodiments, the compositions are formulated into topical skin care compositions. The compositions can be cosmetic compositions. In other aspects, the compositions can be included in a cosmetic vehicle. Non-limiting examples of cosmetic vehicles are disclosed in other sections of this specification and are known to those of skill in the art. Examples of cosmetic vehicles include creams, lotions, and ointments. In other non-limiting embodiments, the compositions of the present invention can be included in skin moisturizing products such as hand, face, or total body moisturizers. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired; the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). In particular embodiments, the composition has a viscosity ranging from 14,000 to 30,000 cps. The compositions in non-limiting aspects can have a pH of about 6 to about 9. In other aspects, the pH can be 1, 2, 3, 4, 5, 6, 7, 8, 9, 10, 11, 12, 13, or 14. In other aspects, the compositions can be sunscreens having a sun protection factor (SPF) of 1, 5, 10, 15, 20, 25, 30, 35, 40, 45, 50, 55, or more.

The composition can have a cosmetically or pharmaceutically elegant feel such a non-oily, non-greasy, non-sticky, non-tacky, and/or silky feel after being applied to skin such as hand skin.

Also disclosed is a method of treating or preventing a skin condition comprising topical application of any one of the compositions described in this specification to skin in need thereof, wherein the topical application of the composition treats the skin condition. In one aspect, the method includes moisturizing skin or treating or preventing the appearing of dry skin, flaky skin, or chapped skin. In other aspects, it is contemplated that the compositions can be used to treat or prevent skin conditions ranging from pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin). In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also contemplated are kits that includes the compositions of the present invention. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

The compositions and methods for their use can "comprise," "consist essentially of," or "consist of" any of the ingredients disclosed throughout the specification. When the transitional phrase "consist(s) essentially of" is used in a claim, the basic and novel characteristic of the claimed composition is its ability to remain stable, moisturize skin, and protect skin from UV radiation, while also having a cosmetically elegant feel.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, skin, hair and nails.

The teems "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the mixtures may not form a solution. The ingredients/components can also exist as undissolved colloidal suspensions.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

In today's image conscious society, people are continually looking for a product that can improve the visual appearance of their skin. For instance, symptoms associated with dry skin (e.g., flaky skin, dried or rough tactile quality, cracked skin, dehydrated skin, itchy skin, or red or erythemic skin) is associated with unattractive skin. Previous attempts to create a composition to treat or prevent dry skin have been meet with numerous drawbacks ranging from compositions having unpleasant tactile properties (e.g., heavy, greasy, or sticky feel), low staying power (e.g., tendency to migrate and pool from point of application or tendency to be easily removed from the skin via being subjected to only one washing), or insufficient moisturization or UV protection capabilities.

The present invention is an effective alternative to the current skin moisturizers on the market. In one non-limiting aspect, the compositions of the present invention is formulated as a stable non-ionic oil-in-water emulsion having water, a combination of non-ionic emulsifiers and non-ionic emulsion stabilizers, a combination of humectant skin conditioning agents, and a combination of UV absorbing agents. This combination of features surprising produces a dermatologically acceptable composition that has a cosmetically elegant feel and is capable of moisturizing skin and protecting the skin from UV radiation. These and other aspect of the present invention are described in further detail below.

A. Water

The oil-in-water emulsions of the present invention include water. One of the benefits of water is that it is capable of producing a composition having a light, non-greasy feel. An additional benefit is that water is a natural ingredient that can hydrate the skin. In one non-limiting aspect of the present invention, the oil-in-water emulsions can include less than 50% (w/w) of water, yet still remain stable and produce a cosmetically elegant feel when applied to skin. The inventor has surprisingly discovered that a combination of non-ionic emulsifiers and non-ionic emulsion stabilizers, a combination of humectant skin conditioning agents, and a combination of UV absorbing agents can effectively produce a stable oil-in-water emulsion have less than 50% (w/w) of water, yet still have a cosmetically elegant feel and effective skin moisturization and UV protection properties.

B. Non-Ionic Emulsifiers and Non-Ionic Emulsion Stabilizers

Non-ionic emulsifiers are neutrally charged molecules that have the ability to emulsify two immiscible phases such as water and oil. Non-ionic emulsion stabilizers are also neutrally charged molecules. These molecules can be used to stabilize an emulsion. Non-limiting examples of non-ionic emulsifiers and stabilizers that can be used in the context of the present invention include those listed in the International Cosmetic Ingredient Dictionary Handbook, $12^{th}$ Edition (2008) and in PCT Publications WO 97/40816 and WO 97/40817, the contents of which are all incorporated by reference.

In particular embodiments, the inventor discovered that a particular combination of non-ionic emulsifiers and stabilizers works well in the context of the disclosed stable oil-in-water emulsions. This combination includes glyceryl stearate, PEG-100 stearate, arachidyl glucoside, and arachidyl alcohol. It was also discovered that a ratio of approximately 18:1 to 23:1 or from 20:1 to 22:1 of the total amount of water (w/w) to the total amount of this particular combination non-ionic emulsifiers and non-ionic emulsion stabilizers works surprisingly well.

C. Humectant Skin Conditioning Agents

Humectant skin conditioning agents include ingredients that are capable of increasing the water content of the top layers of skin by retaining water present in the composition and also absorbing or attracting water from air. Non-limiting examples of humectants that can be used in the context of the present invention include those listed in the International Cosmetic Ingredient Dictionary Handbook, $12^{th}$ Edition (2008), Vol. 3, pages 3236-3239, which is incorporated by reference.

In particular embodiments, the inventor discovered that a particular combination of humectant works well in the context of the disclosed stable oil-in-water emulsions. This combination includes glycereth-26, glycerin, betaine, panthenol, and allantoin. It was also discovered that a ratio of approximately 4:1 to 8:1 or from 5:1 to 7:1 of the total amount of water (w/w) to the total amount of this particular combination humectants works surprisingly well.

D. UV Absorbing Agents

UV absorbing agents are capable of protecting skin from UV radiation (e.g., UVA, UVB, and/or UVC radiation). Non-limiting examples of UV Absorbing Agents that can be used in the context of the present invention include those listed in the International Cosmetic Ingredient Dictionary Handbook, $12^{th}$ Edition (2008), Vol. 3, pages 3236-3239, which is incorporated by reference. Such examples include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (and octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, dibenzoylmethane derivatives (e.g., avobenzone), styrene/acrylates copolymer (e.g., SUNSPHERES™ sold by Rohm and Haas), octocrylene, etc. Non-limiting examples of physical sunblocks include, kaolin, talc, petrolatum and metal oxides (e.g., titanium dioxide and zinc oxide).

In particular embodiments, the inventor discovered that a particular combination of UV absorbing agents well in the context of the disclosed stable oil-in-water emulsions. This combination includes homosalate, octisalate, oxybenzone, avobenzone, octocrylene, and styrene/acrylates copolymer. It was also discovered that a ratio of approximately 2:1 to 3:1 of the total amount of water (w/w) to the total amount of this particular combination of UV absorbing agents (w/w) produces a stable emulsion having an SPF of approximately 30.

E. Compositions of the Present Invention

While particular embodiments and amounts are described throughout this specification, it is contemplated that the compositions of the present invention can include water, a combination of non-ionic emulsifiers and non-ionic emulsion stabilizers, a combination of humectant skin conditioning agents, and a combination of UV absorbing agents can be included in any combination and any amount. Additionally, the compositions can include any number of combinations of additional ingredients described throughout this specification. The concentrations of any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

F. Vehicles

The compositions of the present invention can be incorporated into all types of cosmetically and dermalogically acceptable vehicles. Non-limiting examples of suitable vehicles include creams, lotions, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that ingredients identified throughout this specification, including but not limited to water, the combination of non-ionic emulsifiers and non-ionic emulsion stabilizers, the combination of humectant skin conditioning agents, and the combination of UV absorbing agents can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver the ingredient to skin (see, e.g., U.S. Pat. No. 6,387,398; U.S. Pat. No. 6,203,802; U.S. Pat. No. 5,411,744; Kreuter 1998).

G. Cosmetic Products and Articles of Manufacture

The composition of the present invention can also be used in many cosmetic products including, but not limited to, moisturizing creams or lotions (e.g., hand creams or lotions, face creams or lotions, neck and décolleté creams or lotions, body creams or lotions, etc.), sunscreen products, sunless skin tanning products, hair products, finger nail products, softeners, day lotions, gels, ointments, foundations, night creams, lipsticks, cleansers, toners, masks, skin-whiteners/brighteners, or other known cosmetic products or applications. Additionally, the cosmetic products can be formulated as leave-on or rinse-off products. In certain aspects, the compositions of the present invention are stand-alone products.

H. Additional Ingredients

In addition to the water, the combination of non-ionic emulsifiers and non-ionic emulsion stabilizers, the combination of humectant skin conditioning agents, and the combination of UV absorbing agents disclosed throughout this specification, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, althea officinalis extract, apricot (*prunus armeniaca*) kernel oil, arginine, arginine aspartate, arnica montana extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, calendula officinalis extract, *calendula officinalis oil*, candelilla (*euphorbia cerifera*) wax, canola oil, caprylic/capric triglyceride, cardamon (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, maltitol, matricaria (*chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

b. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

c. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

d. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

e. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

f. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

g. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

I. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Non-Limiting Product Formulation

Non-limiting composition formulated as stable non-ionic oil-in-water emulsion is described in Table 1.

TABLE 1

| Ingredients | % (w/w) |
|---|---|
| Water | 47.6 |
| Homosalate | 5.0 |
| Octisalate | 5.0 |
| Oxybenzone | 4.0 |
| Glycereth-26 | 4.0 |
| Glycerin | 2.985 |
| Avobenzone | 2.0 |
| Octocrylene | 2.0 |
| Styrene/Acrylates Copolymer | 1.72125 |
| Betaine | 1.0 |
| Glyceryl Stearate | 0.9 |
| Arachidyl Alcohol | 0.605 |
| PEG-100 Stearate | 0.6 |
| Arachidyl Glucoside | 0.165 |
| Panthenol | 0.1 |
| Allantoin | 0.08 |
| Excipients* | q.s. |
| TOTAL | 100 |

*Cosmetic or pharmaceutical excipients can be used to fill out the composition to create a desired product (e.g., cream, lotion, etc.), tactile property (e.g., non-oily feel, light weight, silky, etc.), viscosity (e.g., thicker or thinner formulation), and/or a therapeutic effect (e.g., treatment of fine lines and wrinkles, skin-whitening, evening skin tone, increased collagen production, etc.). Non-limiting examples of such excipients that can be used with the Table 1 formulation are known to those having skill in the cosmetic and pharmaceutical field including those disclosed in the present specification (e.g., moisturizing agents, antioxidants, structuring agents, essential and non-essential oils, thickening agents, preservatives, skin lightening agents, silicone containing compounds, vitamins, minerals, pharmaceutical ingredients, fragrances, colors, dyes, chelating agents, botanical extracts, anti-microbial agents, anti-irritants, pH adjusters, exfoliants, etc.).

The above formulation has less than 50% by weight of water and yet remains stable and provides an SPF protection to a user of approximately 30. This formulation includes: (a) a combination of non-ionic emulsifiers (i.e., glyceryl stearate, PEG-100 stearate, and arachidyl glucoside) and non-ionic emulsion stabilizers (e.g., arachidyl alcohol); (b) a combination of humectant skin conditioning agents (i.e., glycereth-26, glycerin, betaine, panthenol, and allantoin); and a combination of UV absorbing agents (i.e., homosalate, octisalate, oxybenzone, avobenzone, octocrylene, and styrene/acrylates copolymer). The ratio of the total amount of water (w/w) to the total amount of the combination non-ionic emulsifiers and non-ionic emulsion stabilizers (w/w) is approximately 21:1; the ratio of the total amount of water (w/w) to the total amount of the combination of humectant skin conditioning agents (w/w) is approximately 6:1; the ratio of the total amount of water (w/w) to the total amount of the combination of UV absorbing agents (w/w) is approximately 2.4:1. These ratios produce a stable emulsion that is effective in moisturizing skin (see below data) while also having aesthetically pleasing tactile properties.

The compositions in Table 1 was prepared by mixing the hydrophilic and hydrophobic ingredients in separate containers at room temperature (20-25° C.). The containers were then added together with continuous mixing under heat (approximately 60-80° C.) until a homogenous mixture was obtained. The mixture was then cooled to room temperature (approximately 20-25° C.).

Example 2

Skin Moisturization Data

The Table 1 composition was tested for its ability to moisturize human skin. Although data is not shown, the composition moisturized human skin.

Example 3

UV Data

The Table 1 composition was tested for its ability to absorb ultra violet radiation. Although data is not shown, the composition exhibited ultra violet absorption characteristics consisting with a rating of a Sun Protection Factor (SPF) of at least 30.

Example 4

Stability Data

The Table 1 composition was confirmed to be stable under a heat stability test.

Example 5

Prophetic Examples

Additional efficacy data points of compositions of the present inventions can be determined by methods known to those of ordinary skill in the art. The following are non-limiting procedures that can be used in the context of the present invention. It should be recognized that other testing procedures can be used, including, for example, objective and subjective procedures.

Skin moisture/hydration can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72 C). Three separate impedance readings can be taken on each side of the face, recorded, and averaged. The T5 setting can be used on the impedance meter which averages the impedance values of every five seconds application to the face. Changes can be reported with statistical variance and significance.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height x-axis).

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control. This test can also be used to confirm the skin exfoliation abilities of the composition (e.g., stain skin and then treat stained skin with composition to determine amount of stain removed over a targeted time period).

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether the product is inducing irritation. The measurements were made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. Skin clarity is defined as L/C where C is chroma and is defined as $(a^2+b^2)^{1/2}$.

All of the compositions and/or methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A non-ionic oil-in water emulsion comprising:
   (a) 40 to 50% by weight of water;
   b. a combination of non-ionic emulsifiers and non-ionic emulsion stabilizers comprising:
   0.8-1% by weight of glyceryl stearate;
   0.5-0.7% by weight of arachidyl alcohol;
   0.5-0.7% by weight of PEG-100 stearate; and
   0.1-0.3% by weight of arachidyl glycoside
   (c) a combination of humectant skin conditioning agents comprising glycereth-26, glycerin, betaine, panthenol, and allantoin; and
   (d) a combination of UV absorbing agents comprising homosalate, octisalate, oxybenzone, avobenzone, octocrylene, and styrene/acrylates copolymer,
   wherein the emulsion is stable and includes an SPF of at least 30.

2. The emulsion of claim 1, wherein the emulsion comprises:
   (a) 45-49% by weight of water;
   (b) 2-3% by weight of the combination of glyceryl stearate, PEG-100 stearate, arachidyl glucoside, and arachidyl alcohol;
   (c) 7-9% by weight of the combination of glycereth-26, glycerin, betaine, panthenol, and allantoin, and
   (d) 18 to 22% by weight of the combination of homosalate, octisalate, oxybenzone, avobenzone, octocrylene, and styrene/acrylates copolymer.

3. The emulsion of claim 1, wherein the emulsion comprises:
   3 to 5% by weight of glycereth-26;
   2 to 4% by weight of glycerin;
   0.1 to 2% by weight of betaine;
   0.01 to 1% by weight of panthenol; and
   0.01 to 1% by weight of allantoin.

4. The emulsion of claim 3, wherein the emulsion comprises:
   4 to 6% by weight of homosalate;
   4 to 6% by weight of octisalate;

3 to 5% by weight of oxybenzone;
1 to 3% by weight of avobenzone;
1 to 3% by weight of octocrylene; and
1 to 3% by weight of styrene/acrylates copolymer.

5. The emulsion of claim 1, wherein:
the ratio of the total amount of water (w/w) to the total amount of the combination non-ionic emulsifiers and non-ionic emulsion stabilizers (w/w) ranges from 18:1 to 23:1 or from 20:1 to 22:1;
the ratio of the total amount of water (w/w) to the total amount of the combination of humectant skin conditioning agents (w/w) ranges from 4:1 to 8:1 or from 5:1 to 7:1; and/or
the ratio of the total amount of water (w/w) to the total amount of the combination of UV absorbing agents (w/w) ranges from 2:1 to 3:1.

6. The emulsion of claim 5, wherein the ratio of the total amount of the combination of humectant skin conditioning agents (w/w) to the total amount of the combination non-ionic emulsifiers and non-ionic emulsion stabilizers (w/w) ranges from 2:1 to 5:1 or from 3:1 to 4:1.

7. The emulsion of claim 6, wherein the ratio of the total amount of the combination of UV absorbing agents (w/w) to the total amount of the combination of humectant skin conditioning agents (w/w) ranges from 1:1 to 4:1 or from 2:1 to 3:1.

8. The emulsion of claim 7, wherein the ratio of the total amount of the combination of UV absorbing agents (w/w) to the total amount of the combination non-ionic emulsifiers and non-ionic emulsion stabilizers (w/w) ranges from 7:1 to 10:1 or from 8:1 to 9:1.

9. The emulsion of claim 1, wherein the composition has a non-oily feel.

10. The emulsion of claim 1, wherein the composition has a silky texture.

11. A method for moisturizing skin comprising topically applying the composition of claim 1 to skin in need thereof.

12. The method of claim 11, wherein the composition is applied to dry or flaky skin.

13. The method of claim 11, wherein the composition moisturizes skin for at least 12 hours after topical application.

14. The method of claim 13, wherein the composition remains on the skin after the skin has been washed at least two times.

15. The method of claim 14, wherein the composition is applied to facial skin.

16. The method of claim 11, wherein the composition has a non-oily feel when applied to skin.

17. The method of claim 11, wherein the composition has a silky texture when applied to skin.

18. A method of treating a skin condition comprising topically applying the composition of claim 1 to skin in need thereof, wherein the topical application treats the skin condition.

* * * * *